United States Patent [19]
Vega

[11] 3,990,447
[45] Nov. 9, 1976

[54] SYSTEM FOR IRRIGATION OF THE HUMAN BLADDER

[76] Inventor: Roger E. Vega, R.D. 6, Kittanning, Pa. 16201

[22] Filed: July 24, 1975

[21] Appl. No.: 598,777

[52] U.S. Cl. .............................. 128/234; 128/349 R
[51] Int. Cl.² ................... A61M 1/00; A61M 25/00
[58] Field of Search .......... 128/234, 227, 276, 230, 128/349 R, 350 R

[56] References Cited
UNITED STATES PATENTS

| | | | |
|---|---|---|---|
| 3,042,042 | 7/1962 | Blanck | 128/276 |
| 3,316,910 | 5/1967 | Davis | 128/227 |
| 3,329,147 | 7/1967 | Barron | 128/230 |
| 3,481,334 | 12/1969 | Diskin et al. | 128/230 |
| 3,513,846 | 5/1970 | Gallo | 128/234 |

Primary Examiner—Lawrence W. Trapp
Attorney, Agent, or Firm—Brown, Murray, Flick & Peckham

[57] ABSTRACT

A closed system is provided for irrigation of the human bladder following surgery, or for other reasons. The system includes a unitary flow control device having a syringe and arranged for making sealed connections to a catheter and to supply and drain lines. Separate flow paths can be established by manipulation of the flow device between the syringe and the catheter, the supply line and the drain line so that the irrigation can be carried out without opening the system at any point and the risk of infection is eliminated.

16 Claims, 12 Drawing Figures

SYSTEM FOR IRRIGATION OF THE HUMAN BLADDER

BACKGROUND OF THE INVENTION

The present invention relates to irrigation of the human bladder, and more particularly to a closed system for irrigating the bladder without the risk of infection.

Irrigation of the bladder is frequently necessary following surgery and is sometimes required because of other conditions, such as bleeding following an injury or due to stones or tumors, or in cases of neurogenic bladder or chronic obstruction. After some surgical procedures, irrigation may be necessary for as long as four or five days and the intervals between treatments can be as short as fifteen minutes immediately following the surgery.

In the conventional procedure, a catheter is inserted into the bladder and remains in place in the patient as long as irrigation is needed. The catheter is connected to a drain bag or container between treatments to allow urine to be discharged. When an irrigation treatment is to be given, the catheter is disconnected from the drain bag and a plunger-type syringe is filled with sterile water, or other fluid suitable for irrigation, and connected to the catheter. The bladder is then irrigated by depressing the plunger of the syringe after which the plunger is retracted to withdraw the fluid from the bladder. The catheter is then disconnected from the syringe and reconnected to the drain bag until time for the next treatment. This frequent opening and closing of the system provides many opportunities for infection, especially in situations such as the first 24 hours following some surgical procedures, such as electrosurgery, where the patient is highly susceptible to infection. Opening and closing the system repeatedly at such times frequently results in infection from the many possible sources of infection such as airborne bacteria, bacteria carried on the hands of nurses or other attendants, and other sources. Heavy preventive doses of antibiotics are sometimes given at great expense, even though such measures do not effectively control the situation.

SUMMARY OF THE INVENTION

The present invention provides a closed system for irrigating the bladder which eliminates the risks of infection discussed above as it is not necessary to open the system when a treatment is to be given.

In accordance with the invention, a unitary flow control device is used which has a body portion to which a syringe is connected and which also has connecting portions for attaching a catheter, a supply line for the sterile water or other fluid to be used, and a drain line. These connections are effectively sealed and remain sealed throughout the time that treatments are necessary, the catheter remaining in place in the patient. The flow control device is arranged so that separate flow paths can be established through it to connect the syringe successively to the supply line, the catheter and the drain line, and also to connect the catheter to the drain line during the periods between treatments. Irrigation of the bladder can then be accomplished by manipulation of the flow control device to establish the required flow paths in the proper sequence without opening the system at any time, so that any risk of infection is avoided.

The flow control device can take various forms. Thus, the flow control device may be a tubular body portion consisting of a suitable length of tubing with the syringe connected to one end of the body. The other end has three branches for connection of the catheter, the supply line and the drain line, respectively. Manually operated clamps are provided on the three branches so that they can be opened and closed as required to establish the necessary flow paths. In another embodiment, the syringe itself includes the body portion and carries the three branches to which the three lines with clamps are connected and operated as in the first embodiment. In still another embodiment, a multiposition valve is used which has a stationary body portion and a relatively rotatable valve element carrying the syringe. The body portion has connections for the catheter, the supply line and drain line, and operation of the valve element aligns the syringe with ports in the body portion to establish the separate flow paths.

BRIEF DESCRIPTION OF THE DRAWINGS

The invention will be more fully understood from the following detailed description, taken in connection with the accompanying drawings, in which.

DESCRIPTION OF THE PREFERRED EMBODIMENT

Figure 1:
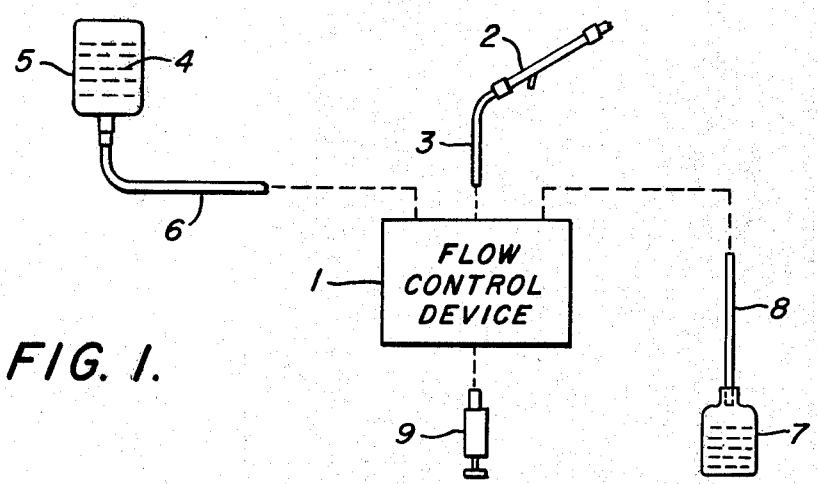
FIG. 1 is a schematic view of the complete system.

As discussed above, the present invention provides a completely closed system for irrigation of the human bladder. FIG. 1 of the drawing shows diagrammatically the complete system. As there shown, the system includes a flow control device 1 which may be a device of any suitable type, such as those disclosed hereinafter, which can be manipulated to establish the required flow paths without opening the system. A catheter 2 is inserted into the patient's bladder and normally remains in place in the patient throughout the entire time during which periodic irrigation of the bladder is necessary. The catheter 2 is connected either directly or by suitable tubing 3 or other connecting means to the control device 1. The sterile water or other liquid 4 which is to be used for irrigation is contained in a reservoir 5 and connected to the flow control device 1 by a supply line 6. The reservoir 5 may be a container of any desired type and is preferably supported in an elevated position, as shown in FIG. 1, so that the liquid 4 is under sufficient hydrostatic pressure to cause it to flow through the system in the desired manner. The necessary liquid 4 may, of course, be provided to the supply line 6 in any desired manner and may be pressurized to the extent necessary by any suitable means. A drain bag or container 7 is also provided which may be of any suitable type and positioned in any convenient location. A drain line 8 is connected to the device 1 to discharge waste fluids to the drain bag 7.

In the use of the system, the catheter 2 is inserted into the bladder of the patient and connected to the flow control device 1 by the line 3. The supply and drain lines 6 and 8 are also connected to the device 1 and a plunger-type syringe 9 is attached, all connections being effectively sealed. The supply line 6 is closed off and the syringe 9 is empty with its plunger depressed, while the line 3 is connected to the drain line 8 to permit the discharge of urine. This is the normal condition of the system between treatments. When a treatment is to be given, the control device 1 is manipulated to close off the drain line 8 and to connect the syringe to the supply line 6. The syringe is filled by retracting the plunger and the supply line is then closed off and the syringe connected to the catheter line 3. The irrigation is performed by depressing the plunger of the syringe to force the fluid into the bladder, and then retracting the plunger to withdraw the fluid. The catheter line 3 is then closed off and the syringe is connected to the drain line 8 and emptied by depressing the plunger. The catheter line 3 is then again connected to the drain line 8 and the system is again in its normal condition until the next treatment. It will be seen that the entire treatment is performed by manipulating the control device 1 to establish the necessary flow paths in the proper sequence without opening the system at any time. The system thus remains closed for as long as irrigation is required, and irrigation treatments can be given at whatever time intervals are desired and over as long a period as necessary without any risk of infection.

Figure 2:
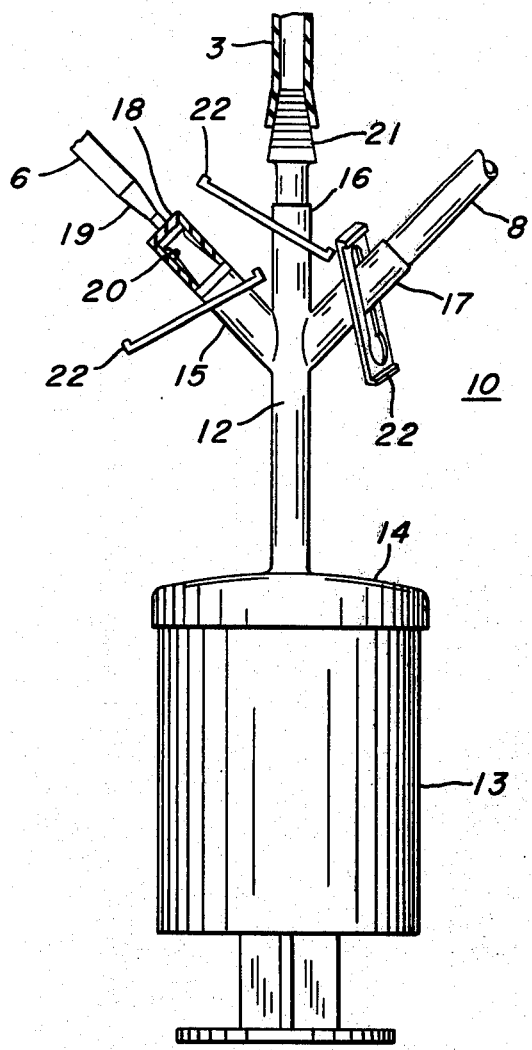
FIG. 2 is a view of a flow control device for use in the system of FIG. 1.

The flow control device 1 may be a device of any suitable type which is capable of operation in the manner described above. A preferred type of control device is shown in FIG. 2. The device 10 there shown has a tubular body portion 12 which may consist of a suitable length of plastic tubing. A plunger-type syringe 13 is connected to one end of the body portion 12, shown as the lower end. The syringe 13 may be of any suitable or conventional type but is shown as being of substantially greater diameter than usual in order to reduce the travel of the plunger so as to minimize any risk of infection resulting from exposure of the plunger when it is withdrawn. The lower end 14 of the tubular body 12 is shown as being enlarged to fit on the nozzle of the syringe 13 with a sealing engagement. Any suitable configuration may be used to make an effective seal between the tube 12 and the syringe 13.

The other or upper end of the body 12 has three branches 15, 16 and 17 extending generally in the opposite direction to the syringe 13. The branches 15, 16 and 17 may be formed integrally with the body 12 or may be secured to it in any suitable manner which effectively seals them in place. The supply line 6 is connected to the branch 15. To facilitate connection and minimize risk of infection, the branch tube 15 may have a rubber latex seal 18 closing its open end and adapted to be penetrated by a sterile hollow needle 19 on the line 6 which makes a sealing engagement with a restricted region 20 of the tube 15. The line 3 of the catheter 2, or the catheter itself, is connected to the branch tube 16 which may have a somewhat conical ribbed tip 21 for secure sealing engagement with the tube 3, or catheter, which may have a flared end for engaging the tip 21. The third branch tube 17 is connected to the drain line 8 and preferably has a flared end in which the line 8 is received with an effective sealing engagement.

The necessary separate flow paths through the flow control device 10 are established by individually opening and closing the three branches 15, 16 and 17. This is preferably done manually by means of clamps 22 on each of the branches. Any suitable type of manually operable clamp may be used, and if desired an additional clamp may be provided on the body portion 12 although this is not always necessary. It will be seen that the flow paths through the device are easily established by manipulation of the clamps 22 to carry out irrigation treatments in the manner previously described without opening the system.

Figure 3:
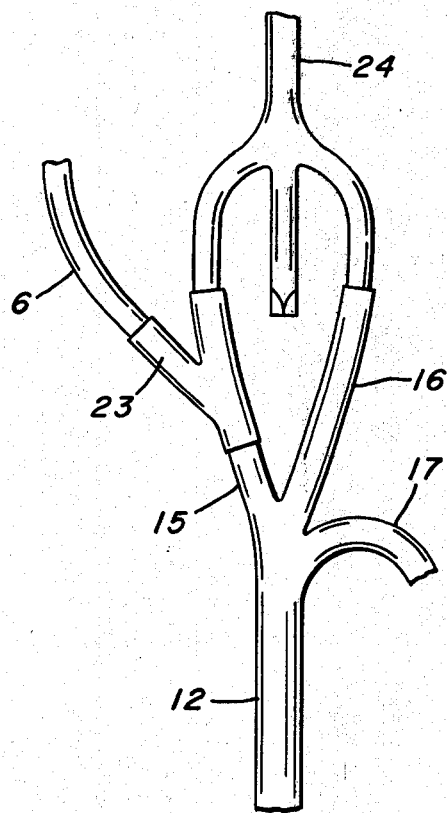
FIG. 3 is a fragmentary view showing a modified embodiment of the device of FIG. 2.

The flow control device 10 provides a simple and inexpensive device, which can easily be made from plastic tubing and which may be disposable because of its low cost. A closed system is thus provided for irrigation of the bladder which prevents any risk of infection but which is simple and easy to operate by manual manipulation. The flow control device can easily be modified, if necessary, for particular purposes. Thus, as shown in FIG. 3, a Y-shaped adapter 23 can be attached to the branch tube 15 for connection of a 3-way Foley catheter 24 to permit continuous bladder irrigation between treatments. The intake port of the catheter 24 is connected to one limb of the adapter 23 while the supply line 6 is connected to the other limb, the connections being effectively sealed by means such as that shown in FIG. 2. With the branch 15 and the body portion 12 closed off by clamps, fluid can flow from the supply line 6 through the adapter 23 to the intake port of the catheter 24. After passage through the bladder, the fluid discharges through the branches 16 and 17 to the drain line 8. The fluid thus flows continuously through the bladder. For intermittent irrigation, the limb of the adapter to which the catheter is connected is closed off by a clamp and the irrigation can then be carried out as described above.

Figure 4:
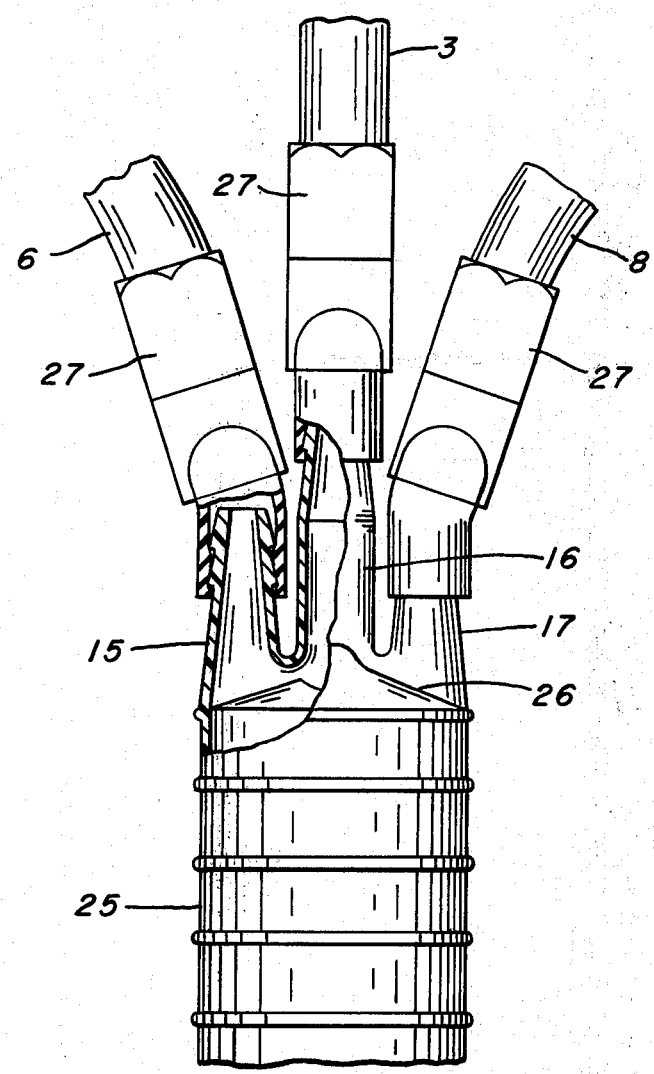
FIG. 4 is a fragmentary view showing another embodiment of the device of FIG. 2.
Figure 6:
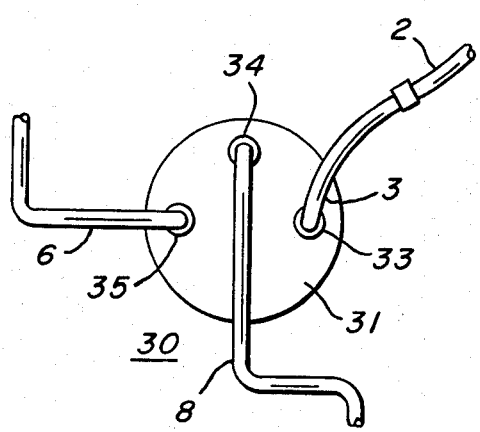
FIG. 6 is an end view of the valve of FIG. 5.

Another embodiment of the flow control device of FIG. 2 is shown in FIG. 4. The device there shown comprises a syringe 25 which is a plunger-type syringe generally as shown in FIG. 2. In the embodiment of FIG. 4, however, the syringe and the body portion are combined in a single integral device which may be molded in one piece of a suitable plastic such as polypropylene. Thus, the syringe 25 has an integral, closed top portion 26 which has the three branches 15, 16 and 17 molded in it. The supply line 6, catheter line 3, and drain line 8 are connected to the branches 15, 16 and 17, respectively, with sealed connections as before, and a clamp 27 of any suitable type is provided for each of the three lines. It will be seen that the operation of this device is the same as that of FIG. 2, as described above, and that it could also be modified for use with the adapter 23 of FIG. 3 in the same way. In the device of FIG. 4, however, the syringe and body portion have been combined so that the top portion 26 of the syringe itself functions as the body portion of the flow control device and an integral, one-piece device is provided which can be manufactured at relatively low cost.

Another type of flow control device suitable for use in the system of FIG. 1 is shown in FIGS. 5-9 and comprises a unitary multiposition valve 30. A particular valve design which has certain advantages is shown in the drawing for the purpose of illustration although other valve designs capable of performing the same functions might be utilized. The valve 30 comprises a stationary body member 31 and a movable valve member 32. The members 31 and 32 are shown as being circular and the member 32 is rotatable with respect to the member 31 about a common central axis. The valve members 31 and 32 may be made of any suitable material, such as stainless steel, which can easily be sterilized and which is not affected by the fluids to which it is exposed. The member 32 may be supported for rotation on the member 31 in any suitable manner, and a seal of any desired type may be provided to prevent leakage.

Figure 7:
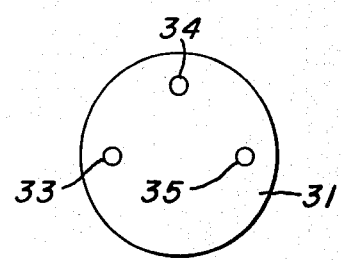
FIG. 7 is a transverse view on the line VII—VII of FIG. 5.
Figure 8:
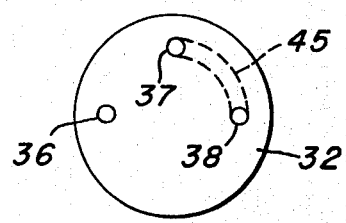
FIG. 8 is a transverse view on the line VIII—VIII of FIG. 5.
Figure 5:
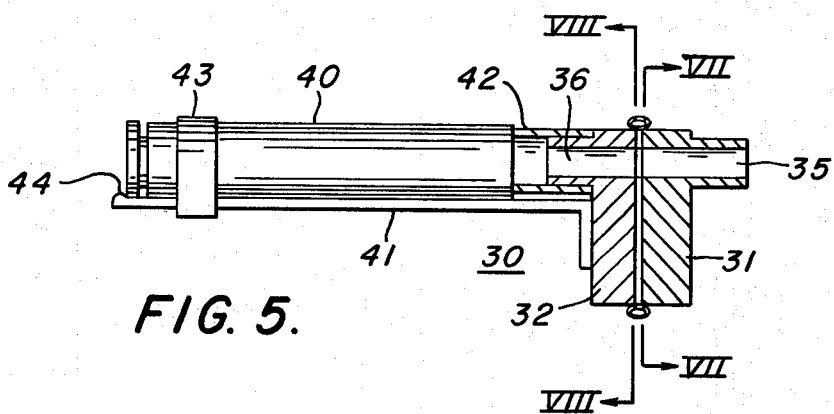
FIG. 5 is a view, partly in side elevation and partly in section, showing a multiposition valve for use in the system of FIG. 1.

The body member 31 has three ports 33, 34 and 35 extending through it. As shown in FIG. 7, these ports are disposed near the periphery of the member 31 and are located 90° apart. Each port has an axial extension adapted for connecting the various lines shown in FIG. 1 to the valve. The port 33 is connected to the catheter line 3 or directly to the catheter 2. The port 34, which is 90° from the port 33, is attached to the drain line 8 and the third port 35 is connected to the supply line 6. The several lines are attached to the respective ports by any type of connection, or connecting means, which makes an effective seal and which can remain in place for the necessary length of time which may be as long as several days.

The movable valve member 32 also has three ports 36, 37 and 38 extending through it. These ports are placed 90° apart and in position to be aligned with the ports 33, 34 and 35 of the stationary member 31 by rotation of the member 32. If desired, index marks or devices 39 may be provided on the two members to indicate their relative positions. A syringe 40 is mounted on the movable valve member 32. The syringe is of the plunger type and is attached to the valve member 32 in alignment with the port 36. The syringe 40 may be mounted in any desired manner, as on a bracket 41 with a sleeve 42 of a suitable resilient material such as neoprene to connect the syringe to the port 36 with a sealed connection. A similar resilient band 43 may be used to hold the syringe in place on the bracket 41, and a lug 44 may be provided at the end of the bracket to lock the plunger of the syringe in the depressed position. The other two ports 37 and 38 of the member 32 are connected together. This connection may be made externally by a piece of tubing 45 connecting the two ports, as shown, or they may be connected in any other desired manner, such as by a passage molded or otherwise formed in the valve member 32.

Figure 9A:
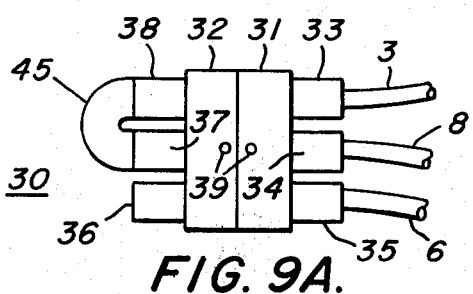
FIGS. 9A, 9B, 9C and 9D are semidiagrammatic plan views showing the valve in its several positions.
Figure 9C:
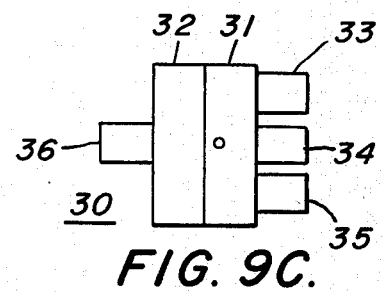
Figure 9B:
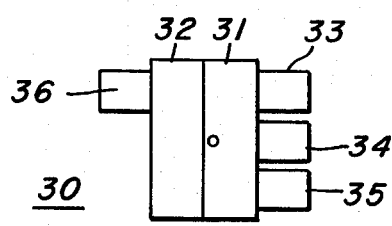

The valve is connected in the system as described above and is initially in a first position shown in FIG. 9A, with the syringe port 36 in alignment with the port 35 so that the syringe is in communication with the supply line 6. The port 33 is aligned with the port 38 in this position of the valve and the ports 34 and 37 are similarly aligned. The catheter is thus connected to the drain line 8 through the connector 45 so that the patient can discharge urine as necessary. This is the normal condition of the system between irrigation treatments. To irrigate the bladder, the plunger of the syringe 40 is retracted to fill the syringe with fluid from the supply line 6. The movable valve member 32 is then rotated 180° to the second position shown in FIG. 9B. In this position, the port 36 is aligned with the port 33 of the body member 31 so that the syringe is directly connected to the catheter, the other ports being closed off. The treatment is then performed by depressing the plunger to force fluid from the syringe into the bladder, after which the plunger is retracted to withdraw the fluid into the syringe. The valve is then moved to the third position shown in FIG. 9C in which the port 36 is aligned with the port 34 to which the drain line 8 is connected and the syringe is emptied by depressing the plunger. The treatment has then been completed and the valve is returned to the first position of FIG. 9A.

Figure 9D:
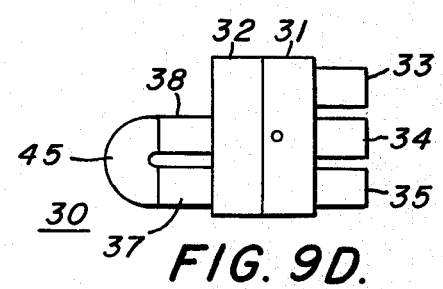

A fourth position of the valve, shown in FIG. 9D, is also available. In this position the supply line 6 is connected to the drain line 8 through the ports 35 and 34 and the connector 45. This position may be utilized to clear the valve if it should be clogged, as by clots, to insure free flow through the valve to the drain line and to insure that the drain line itself is not clogged or obstructed. This flushing action may be utilized as needed to keep the valve clear, but the valve should always be returned to the first position (FIG. 9A) upon completion of a treatment or after flushing of the valve.

It will be noted that the port 33 to which the catheter is connected cannot be connected to the port 35 and supply line 6 in any position of the valve. This is an important feature since there may be substantial pressure in the supply line 6 and if it were connected to the catheter the patient could be subjected to extreme discomfort and, in some cases, a risk of rupturing the bladder might be involved. With the construction shown, however, the spacing and arrangement of the ports are such that the ports 33 and 35 cannot be connected together in any position of the movable member 32. Complete safety is thus assured.

It will now be seen that a system has been provided for irrigation of the human bladder which eliminates any risk of infection since the system remains closed and sealed during the entire period of time in which such treatments are to be given. The frequent opening and closing of the system which has previously been necessary is thus avoided and no opportunity for infection occurs. Any suitable type of unitary flow control device may be used in this system which is capable of operation in the manner described to establish the required flow paths in the proper sequence and without opening the system.

I claim as my invention:

1. Apparatus for irrigating the human bladder comprising a closed system including a unitary flow control device, said flow control device including a syringe and having means for connecting thereto a catheter, a supply line for fluid to be used for irrigation and a drain line, all of said connections being effectively sealed, and manual means for establishing separate flow paths through said device between the syringe and the catheter, the supply line and the drain line without opening the system.

2. The apparatus defined in claim 1 and further including means for establishing a flow path between the catheter and the drain line.

3. Apparatus as defined in claim 1 in which said flow control device is a unitary device having a body portion and including a syringe, said body portion having connecting portions for said catheter, said supply line and said drain line extending therefrom.

4. Apparatus as defined in claim 3 in which said flow control device has a generally tubular body portion, one end of the body portion being adapted for connection of said syringe thereto, and the other end of the body portion having three branches adapted for connection thereto of the catheter, the supply line and the drain line, respectively.

5. Apparatus as defined in claim 4 and including means for individually opening and closing said three branches to control flow of liquid therethrough.

6. Apparatus as defined in claim 5 in which said opening and closing means comprises an individual, manually operated clamp on each of said branches.

7. Apparatus as defined in claim 3 in which said syringe and said body portion constitute a single, integral member.

8. Apparatus as defined in claim 7 in which said syringe has an integral top portion closing the top of the syringe, said top portion having three branches extending therefrom for connection of said catheter, said supply line and said drain line.

9. Apparatus as defined in claim 8 and including manual clamp means for each of said three branches.

10. Apparatus as defined in claim 1 in which said flow control device comprises a multiposition valve having a syringe connected thereto, and having means for separately connecting thereto said catheter, said supply line and said drain line, said valve having a plurality of positions for establishing said flow paths including a first position in which said catheter is connected to said drain line and said syringe is connected to said supply line, a second position in which the syringe is connected to the catheter, and a third position in which the syringe is connected to the drain line.

11. Apparatus as defined in claim 10 in which said valve has a fourth position in which the supply line is connected to the drain line.

12. Apparatus as defined in claim 10 in which the valve means includes means for preventing connection of the supply line to the catheter.

13. Apparatus as defined in claim 10 in which the valve has a stationary body member and a movable member, said body member having three ports therein communicating respectively with said catheter, said supply line and said drain line, said syringe being mounted on said movable member, and connector means on the movable member, said movable member being adapted to be moved between said first, second and third positions to place the syringe in alignment successively with said supply line port, said catheter port and said drain line port, and to place the connector means in alignment with the catheter port and the drain line port in the first position of the movable member.

14. Apparatus as defined in claim 13 in which the movable member has a fourth position in which the connector means is aligned with the supply line port and the drain line port.

15. A syringe for use in a closed system for irrigating the human bladder, said syringe comprising a generally cylindrical portion having a plunger slidably received therein, and a top portion closing the top of the cylindrical portion, said top portion having three tubular branches extending therefrom, said branches being adapted for making sealed connections thereto.

16. A syringe as defined in claim 15 in which said top portion and tubular branches are integral with the cylindrical portion.

* * * * *